US012357616B2

(12) United States Patent
Ait-Tihyaty

(10) Patent No.: US 12,357,616 B2
(45) Date of Patent: Jul. 15, 2025

(54) METHODS OF TREATING MULTIPLE SCLEROSIS

(71) Applicant: Vanda Pharmaceuticals Inc., Washington, DC (US)

(72) Inventor: Maria Ait-Tihyaty, Montreal (CA)

(73) Assignee: Vanda Pharmaceuticals Inc., Washington, DC (US)

(*) Notice: Subject to any disclaimer, the term of this patent is extended or adjusted under 35 U.S.C. 154(b) by 0 days.

(21) Appl. No.: 17/962,714

(22) Filed: Oct. 10, 2022

(65) Prior Publication Data

US 2023/0114486 A1 Apr. 13, 2023

Related U.S. Application Data

(60) Provisional application No. 63/254,385, filed on Oct. 11, 2021.

(51) Int. Cl.
*A61K 31/426* (2006.01)
*A61P 25/28* (2006.01)

(52) U.S. Cl.
CPC ............ *A61K 31/426* (2013.01); *A61P 25/28* (2018.01)

(58) Field of Classification Search
CPC ..... A61K 31/426; A61K 9/0053; A61P 25/28; A61P 21/00
See application file for complete search history.

(56) References Cited

U.S. PATENT DOCUMENTS

| | | | |
|---|---|---|---|
| 4,284,786 A | 8/1981 | Kammerer et al. | |
| 4,959,389 A | 9/1990 | Speiser et al. | |
| 8,232,250 B2 | 7/2012 | Klinger | |
| 10,220,023 B2 | 3/2019 | Dingemanse et al. | |

FOREIGN PATENT DOCUMENTS

| | | |
|---|---|---|
| EP | 0312697 A2 | 4/1989 |
| WO | 00/30622 A2 | 6/2000 |
| WO | 2009/115954 A1 | 9/2009 |
| WO | 2010/022177 A2 | 2/2010 |
| WO | 2010/046835 A1 | 4/2010 |
| WO | 2012/061060 A1 | 5/2012 |
| WO | 2014/152494 A1 | 9/2014 |
| WO | 2021/176070 A1 | 9/2021 |

OTHER PUBLICATIONS

Cosman et al. High-Dose Glucocorticoids in Multiple Sclerosis Patients Exert Direct Effects on the Kidney and the Skeleton, Journal of Bone and Mineral Research, 7, p. 1097-1105. (Year: 1994).*
Freedman, Teriflunomide in relapsing multiple sclerosis: therapeutic utility, Therapeutic Advances in Chronic Disease, 4, 192-205. (Year: 2013).*
Olsson et al, Oral ponesimod in relapsing-remitting multiple sclerosis: a randomised phase II trial, J Neurol Neurosurg Psychiatry, 85, p. 1198-1209. (Year: 2014).*
Correction to Olsson in (W) above. (Year: 2019).*
Andersson et al. Glucocorticosteroid therapy for multiple sclerosis: A critical review. (Journal of Neurological Sciences, 160, 16-25). (Year: 1998).*
Achiron et al., "COVID-19 Vaccination in Patients with Multiple Sclerosis: What We have Learnt by Feb. 2021", Multiple Sclerosis Journal, Apr. 15, 2021, vol. 27, No. 6, pp. 864-870.
Achiron et al., "Humoral Immune Response to COVID-19 mRNA Vaccine in Patients with Multiple Sclerosis Treated with High-Efficacy Disease-Modifying Therapies", Ther. Adv. Neurol. Disord., 2021, vol. 14, pp. 1-8.
Anderson, "Teriflunomide Slows Brain Volume Loss in MS", Oct. 21, 2015, pp. 1-3.
Anonimous: "Managing your relapses", MS Society, retrieved from https://www.mssociety.org. uk/care-and-support/resources-and-publications/publications-search/managing-a-relapse-booklet, Nov. 2019, pp. 1-48.
Anonimous: "Package leaflet: Information for the patient—Ponesimod", retrieved from https://www.medicines.org.uk/emc/files/pil.12799.pdf, retrieved on Jan. 17, 2023, pp. 1-10.
Anonimous: "Ponesimod (Oral)", Retrieved from https://web.archive.org/web/20210913052832/https://www.drugs.com/cons/ponesimod.html, Dec. 24, 2020, pp. 1-14.
Anonimous: "Ponesimod—Anwendung, Wirkung, Nebenwirkungen I Gelbe Liste", Gelbe Liste , Retrieved from https://www.gelbe-liste.de/wirkstoffe/ Ponesimod_56402, Retrieved on Jan. 10, 2023, pp. 1-5.
Author unknown, "Barriers to paediatric switching to second-line ART", vol. 6, Feb. 2019, e71-e72.
Boehler et al., "Absolute Bioavailability of Ponesimod, a Selective S1P1 Receptor Modulator, in Healthy Male Subjects", European Journal of Drug Metabolism and Pharmacokinetics, 2017, vol. 42(1), 129-134.
Bolli et al., "2-imino-thiazolidin-4-one derivatives as potent, orally active S1P1 receptor agonists", J. Med. Chem., May 27, 2010, vol. 53(10), 4198-4211.
Brossard et al., "Multiple-dose tolerability, pharmacokinetics, and pharmacodynamics of ponesimod, an S1P receptor modulator: Favorable impact of dose up-titration", J. Clin. Pharmacol., 2014, vol. 54(2), 179-188.
Brossard et al., "Pharmacokinetics and pharmacodynamics of ponesimod, a selective S1P1 receptor modulator, in the first-in-human study", Br. J. Clin. Pharmacol., Dec. 2013, 76(6), 888-896.
Cohen et al., "Mechanisms of fingolimod's efficacy and adverse effects in multiple sclerosis", Ann. Neurol., 2011, vol. 69(5), 759-777.
Cohen et al., "Oral fingolimod or intramuscular interferon for relapsing multiple sclerosis", N. Engl. J. Med., 2010, vol. 362(5), 402-415.
Confavreux et al., "Oral teriflunomideforpatients with relapsing multiple sclerosis (TOWER): a randomised, double-blind, placebo-controlled, phase 3 trial", Lancet Neurol., 2014, vol. 13, No. 3, pp. 247-256.

(Continued)

*Primary Examiner* — Joseph K McKane
*Assistant Examiner* — Meghan C Heasley
(74) *Attorney, Agent, or Firm* — Hoffman Warnick LLC

(57) ABSTRACT

The disclosure relates to methods of treating multiple sclerosis. In certain aspects, methods of reducing corticosteroid use in a patient with multiple sclerosis are disclosed.

13 Claims, 9 Drawing Sheets

(56) References Cited

OTHER PUBLICATIONS

Confavreux et al., "Tower Trial Group Oral Teriflunomide for patients with relapsing multiple sclerosis (TOWER): a randomized double-blind, placebo-controlled, phase 3 trial", Lancet Neurol., Mar. 2014, 13(3), 247-256.

D'Ambrosio et al., "Differential effects of ponesimod, a selective S1P1 receptor modulator, on blood-circulating human T cell subpopulations", Immunopharmacol. Immunotoxicol., 2015, vol. 37(1), 103-109.

D'Ambrosio et al., "Therapeutic Advances in Chronic Disease Ponesimod, a selective SIPI receptor modulator: a potential treatment for multiple sclerosis and other immune-mediated diseases", Ther. Adv. Chronic Dis., Jan. 2016, vol. 7, No. 1, 18-33.

D'Ambrosio et al, "Ponesimod, a selective S1P1 receptor modulator: a potential treatment for multiple sclerosis and other immune-mediated diseases", Therapeutic Advances in Chronic Disease, vol. 7(1), 2016, 18-33.

De Stefano et al., "Establishing Pathological cut-offs of brain atrophy rates in multiple sclerosis", J. Neurol Neurosurg Psychiatry, 2016, vol. 87, pp. 93-99.

European Medicines Agency, "Guidelines on clinical investigation of medicinal products for the treatment of Multiple Sclerosis", Mar. 26, 2015, EMA/CHMP/771815/2011, Rev. 2, Committee for Medicinal Products for Human Use (CHMP).

FDA, "Determining Whether to Submit an ANDA or a 505(b)(2) Application Guidance for Industry", U.S. Department of Health and Human Services, Oct. 2017, pp. 1-14.

Gatfield et al., "Sphingosine-1-Phosphate (S1P) Displays Sustained S1P Receptor Agonism and Signaling through S1P Lyase-dependent Receptor Recycling", Cell Signal., Jul. 2014, vol. 26(7), 1576-1588.

Giorgio et al., "Cognition in multiple sclerosis: relevance of lesions, brain atrophy and proton MR spectroscopy," Neurol Sci, vol. 31, Issue 2, 2010, pp. 245-248.

Guerard et al., "Effect of Hepatic or Renal Impairment on the Pharmacokinetics, Safety, and Tolerability of Ponesimod, a Selective S1P1 Receptor Modulator", Basic Clin. Pharmacol. Toxicol., Article 2016, vol. 118, 356-368.

Handbook of Pharmaceutical Salts, Properties, Selection and Use, P. Heinrich Stahl, Camille G. Wermuth (Eds). Wiley-VCH, 2008 and Pharmaceutical Salts and Co-Crystals, Johan Wouters and Luc Quere (Eds.), RSC Publishing, 2012.

Havrdova et al., "Efficacy and safety of 2 doses of ponesimod (10 and 20 mg o.d.): Interim analysis of a phase II extension trial in relapsing-remitting multiple sclerosi", Oct. 2017—Poster presented; ECTRIMS Online Library, Oct. 27, 2017; 200806. Abstract No. P1151.

Havrdova et al., "Efficacy and safety of 2 doses of ponesimod (10 and 20 mg once daily): Interim analysis of a Phase II extension trial in relapsing-remitting multiple sclerosis", Encore poster presented at AAN Apr. 21-27, 2018, Los Angeles, CA.

Heinrich et al., "Handbook of Pharmaceutical Salts, Properties, Selection and Use", Wiley-VCH, 2008, pp. 1-3.

Hoch et al., "Clinical pharmacology of ponesimod, a selective S1P(1) receptor modulator, after up-titration to supratherapeutic doses in healthy subjects", Eur. J. Pharm. Sci., 2014, vol. 63, 147-153.

Hoch et al., "Effect of ponesimod, a selective S1P1 receptor modulator, on the QT interval in healthy individuals", Basic Clin. Pharmacol. Toxicol., May 2015, vol. 116(5), 429-437.

Hudgens et al., "Development and Validation of the FSIQ-RMS: A New Patient-Reported questionnaire to Assess Symptoms and Impacts of Fatigue in Relapsing Multiple Sclerosis", Value Health, Apr. 2019, 22(4), 453-466.

Huwiler et al., "New players on the center stage: Sphingosine 1-phosphate and its receptors as drug targets", J. Biochem. Pharmacol. Review, 2008, vol. 75(10), 1893-1900.

Janssen Pharmaceutical Companies of Johnson & Johnson, "New Head-to-Head Phase 3 Study Data Show Ponesimod Superiority Versus Aubagio (teriflunomide) 14mg in Adults with Relapsing Multiple Sclerosis (MS)", Sep. 11, 2019, pp. 1-6.

Janssen Pharmaceutical Companies, "PonvoryTM (ponesimod) tablets, for oral use", 2021, pp. 1-34.

Janssen Showcases Recent Data in Relapsing Multiple Sclerosis at the 2021 European Committee for Treatment and Research in Multiple Sclerosis Congress, CISION PR Newswire, retrieved from https://www.prnewswire.com/news-releases/janssen-showcases-recent-data-in-relapsing-multiple-sclerosis-at-the-2021-european-committee-for-treatment-and-research-in-multiple-sclerosis-congress-301387378.html, Sep. 29, 2021, pp. 1-13.

Juif et al., "Biocomparison of three formulations of the S1P1 receptor modulator ponesimod in healthy subjects", Drugs in R&D., Jun. 2015, 15(2), 203-210.

Juif et al., "Clinical pharmacology, efficacy, and safety aspects of sphingosine-1-phosphate receptor modulators", Expert Opin. Drug Metab. Toxicol., Aug. 2016, vol. 12(8), 879-895. Epub. Jun. 13, 2016.

Juif et al., "Mitigation of Initial Cardiodynamic Effects of the S1P1 Receptor Modulator Ponesimod Using a Novel Up-Titration Regimen", Journal of Clinical Pharmacology, 2016, vol. 57(3), 401-410.

Jurcevic et al., "Effects of multiple-dose ponesimod, a selective S1P(1) receptor modulator, on lymphocyte subsets in healthy humans", Drug Des. Devel. Ther., Dec. 28, 2016, vol. 11, 123-131.

Kappos et al., "A Placebo-Controlled Trial of Oral Fingolimod in Relapsing Multiple Sclerosis", N. Engl. J. Med., 2010, vol. 362(5), 387-401.

Kappos et al., "Effect of oral ponesimod on clinical disease activity and MRI-based outcomes in patients with relapsing multiple sclerosis: Phase 3 OPTIMUM study," Multiple sclerosis journal, vol. 26, 2020, pp. 151-152.

Kappos et al., "Oral fingolimod (FTY720) for relapsing multiple sclerosis", N. Engl. J. Med., 2006, 355(11), 1124-1140.

Kappos et al., "Ponesimod Compared With Teriflunomide in Patients With Relapsing Multiple Sclerosis in the Active-Comparator Phase 3 OPTIMUM Study : A Randomized Clinical Trial", JAMA Neurology, vol. 78, No. 5, Mar. 29, 2021, pp. 558-567.

Kappos et al., "The POINT study: a randomized, double-blind, parallel-group, add-on, superiority phase 3 study to compare the efficacy and safety of ponesimod to placebo in subjects with active relapsing multiple sclerosis who are treated with dimethyl fumarate", Poster presented at ECTRIMS (European Committee for Treatment and Research in Multiple Sclerosis), Citation for abstract: ECTRIMS Online Library, Oct. 10, 2018, 228412. Abstract No. P568.

Keown, "Janssen's Ponesimod Finds Success in Head-to-Head Multiple Sclerosis Trial", Jul. 26, 2019, pp. 1-4.

Kihara et al., "Ponesimod inhibits astrocyte-mediated neuroinflammation and protects against cingulum demyelination via S1P1-selective modulation," Sage Publications Abstracts Multiple Sclerosis Journal, Oct. 1, 2021, 1-13.

Krause et al., "Modeling clinical efficacy of the S1P receptor modulator ponesimod in psoriasis", J. Dermatol. Sci., Feb. 2018, vol. 89(2), 136-145, Epub Nov. 20, 2017.

Krause et al., "Population pharmacokinetics and pharmacodynamics of ponesimod, a selective S1P1 receptor modulator", J. Pharmacokinet. Pharmacodyn., Jun. 2014, vol. 41(3), 261-278.

LeBert et al., "Highly Functional Virus-Specific Cellular Immune Response in Asymptomatic SARS-CoV-2 infection", J. Exp. Med., 2021, vol. 218, No. 5, e20202617, pp. 1-17.

Lott et al., "Impact of Demographics, Organ Impairment, Disease, Formulation, and Food on the Pharmacokinetics of the Selective S1P(1) Receptor Modulator Ponesimod Based on 13 Clinical Studies", Clin. Pharmacokinet., Apr. 2017, vol. 56(4), 395-408.

Lott et al., "Modeling the Effect of the Selective S1P1 Receptor Modulator Ponesimod on Subsets of Blood Lymphocytes Pharmaceutical Research", 2017, 34(3), 599-609.

Lott et al., "Modeling Tolerance Development for the Effect on Heart Rate of the Selective S1P1 Receptor Modulator Ponesimod", Clin. Pharmacol. Ther., Jun. 2018, 103(6), 1083-1092, Epub Oct. 27, 2017.

Lott et al., "Population pharmacokinetics of ponesimod and its primary metabolites in healthy and organ-impaired subjects", Eur. J. Pharm. Sci., Jun. 30, 2016, 89, 83-93, Epub Apr. 22, 2016.

(56) References Cited

OTHER PUBLICATIONS

Lublin FD, "Disease activity free status in MS", Mult Scler Relat Disord., Jan. 2012, 1(1), 6-7.

O'Connor et al., "Randomized Trial of Oral Teriflunomide for Relapsing Multiple Sclerosis", New England J. Med., 2011, 365, 1293-1230.

Pharmaceutical Salts and Co-crystals, Johan Wouters and Luc Qur (Eds.), RSC Publishing, 2012.

Piali et al., "The selective sphingosine 1-phosphate receptor 1 agonist ponesimod protects against lymphocyte-mediated tissue inflammation", J. Pharmacol. Exp. Ther., May 2011, vol. 337(2), 547-556.

Polman et al., "Diagnostic criteria for multiple sclerosis: 2010 Revisions in the McDonald criteria", Ann. Neurol., 2011, 69(2), 292-302.

Pouzol et al., "Complete resolution of clinical signs and synergism of the combination ponesimod-dimethyl fumarate in rat models of multiple sclerosis". Encore poster presented at AAN, Apr. 1-27, 2018, Los Angeles, CA.

Pouzol et al., "Therapeutic Potential of Ponesimod Alone and in Combination with Dimethyl Fumarate in Experimental Models of Multiple Sclerosis", Innov. Clin. Neurosci., Mar. 1, 2019, 16(3-4), 22-30.

Pozzilli et al., "Maintenance of efficacy, safety and tolerability of ponesimod in patients with relapsing-remitting multiple sclerosis: phase II extension study", Poster presentation at ECTRIMS (2013) European Committee for Treatment & Research in Multiple Sclerosis—29th Congress.

Rey et al., "Desensitization by progressive up-titration prevents first-dose effects on the heart: guinea pig study with ponesimod, a selective S1P1 receptor modulator", PLoS One, Sep. 12, 2013, vol. 8 Issue 9, e74285.

Reyes et al., "Effects of Ethnicity and Sex on the Pharmacokinetics and Pharmacodynamics of the Selective Sphingosine-1-Phosphate Receptor 1 Modulator Ponesimod: A Clinical Study in Japanese and Caucasian Subjects", Pharmacology, Nov. 14, 2014, vol. 94 (5-6), 223-229.

Reyes et al., "Effects of ponesimod, a selective S1P1 receptor modulator, on the pharmacokinetics of a hormonal combination contraceptive", Eur. J. Clin. Pharmacol., Mar. 2014, vol. 70(3), 287-293.

Reyes et al., "Mass balance, pharmacokinetics and metabolism of the selective S1P receptor modulator ponesimod in humans", Xenobiotica, Sep. 2014, 4, vol. 45, 1-11.

Scherz et al., "Three different up-titration regimens of ponesimod, an S1P1 receptor modulator, in healthy subjects", The Journal of Clinical Pharmacology, Jun. 2015, vol. 55(6), 688-697.

Sobel et al., "FTY720-P activates Sphingosine-1-phosphate receptor 2 and selectively couples to Ga12/13/Rho/ROCK to induce myofibroblast contraction", Mol. Pharmacol., Jun. 2015, vol. 87(6), 916-927.

Sobel et al., "Sphingosine 1-phosphate (S1P) receptor agonists mediate pro-fibrotic responses in normal human lung fibroblasts via S1P2 and S1P3 receptors and Smad-independent signaling", J. Biol. Chem. 2013 May 24, 2013, vol. 288(21), 14839-14851.

The Author(s), published by Elsevier Ltd., "Incidence of switching to second-line antiretroviral therapy and associated factors in children with HIV: an international cohort collaboration", vol. 6, Feb. 2019, e105-e115.

U.S National Library of Medicine: "Oral Ponesimod Versus Teriflunomide in Relapsing Multiple Sclerosis", Apr. 24, 2015, Retrieved from https://clinicaltrials.gov/ct2/show/study/NCT02425644.

Ufer et al., "Impact of siponimod on vaccination response in a randomized, placebo-controlled study", 2017, 1-9.

Vaclavkova et al., "Oral ponesimod in patients with chronic plaque psoriasis: a randomised, double-blind, placebo-controlled phase 2 trial", Lancet, Dec. 6, 2014, vol. 384(9959), 2036-2045, Epub Aug. 10, 2014.

Wouters et al., "Pharmaceutical Salts and Co-crystals", RSC Publishing, 2012, pp. 1-9.

You et al., "Therapeutic use of a selective S1P1 receptor modulator ponesimod in autoimmune diabetes", PLoS One, Oct. 24, 2013, vol. 8(10): e77296.

Zhang et al., "Ponesimod protects against neuronal death by suppressing the activation of A1 astrocytes in early brain injury after experimental subarachnoid hemorrhage", J. Neurochem., Aug. 2021, 158(4), 880-897, doi: 10.1111/jnc.15457. Epub Jul. 16, 2021.

Freedman et al., "Comparing outcomes from clinical studies of oral disease-modifying therapies (dimethyl fumarate, fingolimod, and teriflunomide) in relapsing MS: Assessing absolute differences using a number needed to treat analysis," Multiple Sclerosis and Related Disorders 10: 204-212 (2016).

Leist et al., "Teriflunomide shows consistent clinical efficacy on severe relapses across TEMSO and TOWER: 2 phase 3 trials," Value in Health 18: A279-280 (2015).

\* cited by examiner

METHODS OF TREATING MULTIPLE SCLEROSIS

CROSS-REFERENCE TO RELATED APPLICATIONS

This application claims the benefit of U.S. Provisional Patent Application No. 63/254,385, filed Oct. 11, 2021, the disclosure of which is incorporated by reference herein.

TECHNICAL FIELD

The present disclosure relates to methods of treating multiple sclerosis.

BACKGROUND

Multiple sclerosis (MS) is a chronic autoimmune inflammatory disease of the central nervous system affecting approximately 2.5 million people worldwide. The disease is clinically perceived by relapses and progressive loss of neurological function, primarily attributed to demyelination, axonal loss, and gliosis culminating in long-term multifocal sclerotic plaques in the brain and spinal cord leading to neurological impairment and severe disability. The two main subtypes of MS are relapsing forms of MS (RMS) which represent 85% of MS patients and include relapsing-remitting disease (RRMS), clinically isolated syndrome, and active secondary progressive disease; and primary progressive MS (PPMS) which affects only 15% of MS patients.

Relapses are defined as newly appearing neurological symptoms in the absence of fever or infections that last for more than 24 hours. Relapses may fully recover over days or weeks or lead to persistent residual deficits and accumulation of disability.

The natural history of MS is usually divided into two partially overlapping phases, a predominantly inflammatory phase and a predominantly degenerative phase: after an initial phase of relapsing remitting MS, driven by inflammatory mechanism, patients experience a secondary progressive MS characterized by continuous worsening of symptoms independent of the occurrence of relapses, the degenerative phase of MS. Most currently available disease-modifying treatments (DMTs) address the inflammatory phase of MS and are less efficacious in the degenerative phase.

Current medical practice encourages early intervention with disease-modifying treatments, with the intent of optimizing long-term clinical outcomes.

Key objectives in the management of MS are reducing the rate of relapses and preventing or at least delaying disease progression. Most of the disease-modifying drugs approved for MS have to be administered by injection or infusion (subcutaneous [s.c.], intramuscular [i.m.], or intravenous [i.v.] route). Recently, new disease-modifying drugs administered orally have been approved for RMS.

The following injectable drugs have been approved in at least one country for the treatment of MS:
- Interferon (IFN) β-1a 30 mcg i.m. once weekly (Avonex®)
- IFN β-1a 22 or 44 mcg s.c. 3 times weekly (Rebif®)
- IFN β-1b 250 mcg s.c. every other day (Betaferon®, Extavia®)
- Pegylated IFN β-1a 125 mcg subcutaneously every 2 weeks (Plegridy®)
- Glatiramer acetate 20 mg s.c. once a day (o.d.) or 40 mg subcutaneously 3 times weekly (Copaxone®)
- Glatiramer acetate 20 mg s.c. o.d. (Glatopa®)
- Natalizumab 300 mg i.v. every 4 weeks (Tysabri®)
- Mitoxantrone i.v. every 3 months (Novantrone®)
- Alemtuzumab concentrate for solution for infusion, 12 mg alemtuzumab in 1.2 mL (10 mg/mL) (Lemtrada®)

Several oral drugs have also been approved for MS:
- Fingolimod 0.5 mg orally o.d. (Gilenya®)
- Teriflunomide 7 mg, 14 mg o.d. (Aubagio®)
- Dimethyl fumarate (BG-12) gastro-resistant hard capsules 120/240 mg twice daily (Tecfidera®)
- Cladribine 40 to 100 mg orally per treatment week (Mavenclad®)

Sphingosine-1-phosphate (SIP) plays a central role in lymphocyte trafficking. SIP is synthesized and secreted by many cell types, including platelets, erythrocytes, and mast cells, and elicits a variety of physiological responses. Lymphocyte egress from primary and secondary lymphoid organs is dependent on the S1P1 receptor. S1P1 receptor modulators block lymphocyte migration out of lymphoid tissue into the lymphatic and vascular circulation, thereby reducing peripheral lymphocyte counts and preventing lymphocyte recruitment to sites of inflammation. Following withdrawal of an S1P1 receptor agonist, the functional lymphocytes return to the circulation from their sites of sequestration. Other functions that do not rely on homing mechanisms, such as antibody generation by B lymphocytes, first-line immunological protection by granulocytes and monocytes, and antigen-dependent T-cell activation and expansion, are not affected by this mechanism.

S1P itself induces pleiotropic effects, which are mediated by a family of five G protein-coupled receptors, S1P1-S1P5, located on endothelial cells, vascular and cardiac smooth muscle cells, and cardiac myocytes. The first SIP receptor modulator, fingolimod (FTY720, Gilenya®), which has been approved by the FDA and the EMA for the treatment of MS, is not selective for the S1P1 receptor but interacts with S1P3, S1P4, and S1P5.

Ponesimod, an iminothiazolidinone derivative, is an orally active, selective modulator of the S1P1 that induces a rapid, dose-dependent, and reversible reduction in peripheral blood lymphocyte count by blocking the egress of lymphocytes from lymphoid organs. T and B cells are most sensitive to ponesimod mediated sequestration. In contrast, monocyte, natural killer (NK) cell and neutrophil counts are not reduced by ponesimod. Ponesimod is commercially available as PONVORY™, a once-daily oral medication. In the United States the Food and Drug Administration (FDA) has approved PONVORY™ to treat adults with relapsing forms of multiple sclerosis (MS), to include clinically isolated syndrome, relapsing-remitting disease, and active secondary progressive disease.

Therapy with systemic corticosteroids (SCS) is commonly used for acute treatment of relapses in patients with RMS. However, use of high doses of SCS can lead to unwanted adverse events and tolerability issues. Prolonged treatment can also lead to steroid resistance and may have negative impacts on remyelination. Accordingly, there is a need for treatment options that reduce the number of corticosteroid treatments and/or lower the required dose of corticosteroid needed to manage RMS.

SUMMARY

In some aspects, the present disclosure is directed to methods of reducing corticosteroid use in a patient with multiple sclerosis, comprising administering ponesimod to the patient using a regimen that is effective to reduce corticosteroid use.

In other aspects, the disclosure is directed to methods of reducing corticosteroid use in a patient with multiple sclerosis, comprising administering ponesimod to the patient using a regimen that is effective to reduce corticosteroid use relative to a patient population at substantially the same level of disease progression receiving a standard of care treatment that does not comprise ponesimod.

In some aspects, the present disclosure is directed to ponesimod for use in methods of reducing corticosteroid use in a patient with multiple sclerosis, wherein said methods comprise administrating ponesimod to the patient using a regimen that is effective to reduce corticosteroid use.

In other aspects, the present disclosure is directed to ponesimod for use in methods of reducing corticosteroid use in a patient with multiple sclerosis, wherein said methods comprise administrating ponesimod to the patient using a regimen that is effective to reduce corticosteroid use relative to a patient population at substantially the same level of disease progression receiving a standard of care treatment that does not comprise ponesimod.

In some aspects, the present disclosure is directed to use of ponesimod in the manufacture of a medicament for reducing corticosteroid use in a patient with multiple sclerosis, wherein said medicament is adapted to be administered using a regimen that is effective to reduce corticosteroid use.

In other aspects, the present disclosure is directed to use of ponesimod in the manufacture of a medicament for reducing corticosteroid use in a patient with multiple sclerosis, wherein said medicament is adapted to be administered using a regimen that is effective to reduce corticosteroid use relative to a patient population at substantially the same level of disease progression receiving a standard of care treatment that does not comprise ponesimod.

In addition, the disclosure is directed to pharmaceutical products comprising ponesimod, wherein the pharmaceutical product is packaged and the package includes instructions for administering ponesimod to a human patient suffering from multiple sclerosis in a regimen that is effective to reduce corticosteroid use in the management of the multiple sclerosis.

BRIEF DESCRIPTION OF THE DRAWINGS

FIG. 4-A shows the proportion of patients receiving ≥1 concomitant SCS for treatment of relapse (between study treatment start and EOS). FIG. 4-B shows the accumulated steroid dose for treatment of relapse.

FIG. 5-A shows the proportion of patients receiving ≥1 concomitant SCS for treatment of relapse between study treatment start and EOS. FIG. 5-B shows the accumulated steroid dose for treatment of relapse.

FIG. 6-A shows the proportion of patients receiving ≥1 concomitant SCS for treatment of relapse between study treatment start and EOS. FIG. 6-B shows the accumulated steroid dose for treatment of relapse.

DETAILED DESCRIPTION OF ILLUSTRATIVE EMBODIMENTS

Figure 1:
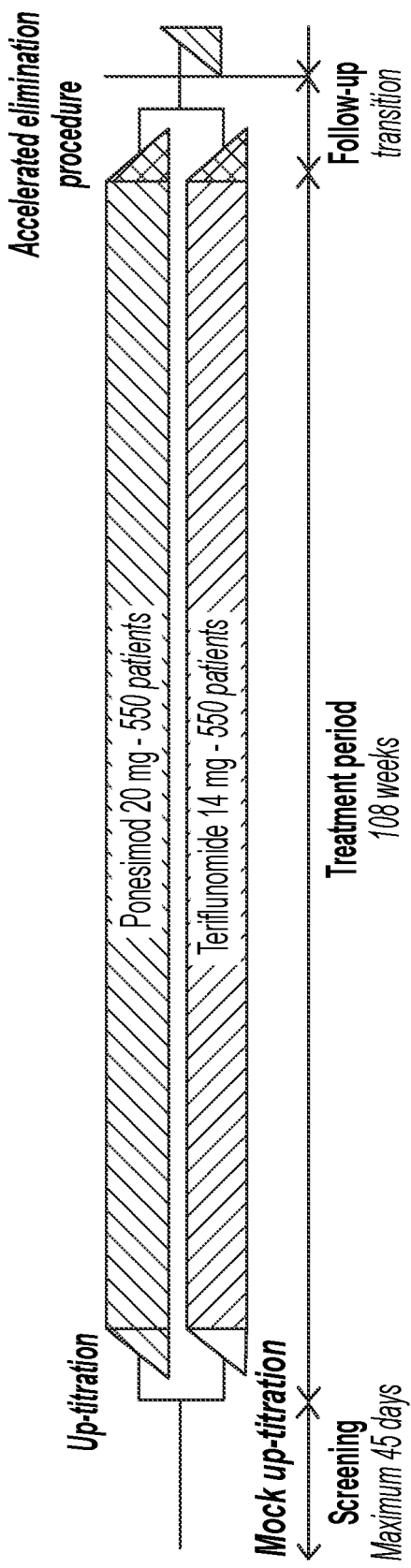
FIG. 1 depicts the OPTIMUM study design.

In the present disclosure the singular forms "a", "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the disclosure which are, for clarity, described herein in the context of separate embodiments, may also be provided in combination in a single embodiment. That is, unless obviously incompatible or excluded, each individual embodiment is deemed to be combinable with any other embodiments and such a combination is considered to be another embodiment. Conversely, various features of the disclosure that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

In some aspects, the present disclosure is directed to methods of reducing corticosteroid use in a patient with multiple sclerosis, comprising administering ponesimod to the patient using a regimen that is effective to reduce corticosteroid use.

In some aspects, the present disclosure is directed to methods of reducing corticosteroid use in a patient with multiple sclerosis, comprising administering ponesimod to the patient using a regimen that is effective to reduce corticosteroid use relative to a patient population at substantially the same level of disease progression receiving a standard of care treatment that does not comprise ponesimod.

It should be understood that references herein to methods of treatment (e.g., methods of reducing corticosteroid use in a patient with multiple sclerosis, comprising administering ponesimod to the patient using a regimen that is effective to reduce corticosteroid use), should also be interpreted as references to:

ponesimod or formulations thereof for use in methods of treatment (e.g., methods for reducing corticosteroid use in a patient with multiple sclerosis); and/or the use of ponesimod or formulations thereof in the manufacture of a medicament for reducing corticosteroid use in a patient with multiple sclerosis.

Typical corticosteroids, include, for example, glucocorticoid, methylprednisone, methylprednisone sodium succinate, dexamethasone, hydrocortisone, prednisolone, prednisolone sodium succinate, and/or prednisone. In certain embodiments, the corticosteroid is glucocorticoid. In certain embodiments, the corticosteroid is methylprednisone. In certain embodiments, the corticosteroid is methylprednisone sodium succinate. In certain embodiments, the corticosteroid is dexamethasone. In certain embodiments, the corticosteroid is hydrocortisone. In certain embodiments, the corticosteroid is prednisolone. In certain embodiments, the corticosteroid is prednisolone sodium succinate. In certain embodiments, the corticosteroid is prednisone. In certain embodiments, the corticosteroid is a combination of any of the corticosteroids disclosed herein.

The ponesimod treatment regimens disclosed herein reduce the number of corticosteroid treatments and/or lower the required dose of corticosteroid needed to manage RMS, including relative to the absence of treatment with ponesimod and/or relative to a patient population at substantially the same level of disease progression receiving a standard of care treatment that does not comprise ponesimod (see Example 1 for exemplary patient population).

In certain embodiments, the reduction of corticosteroid use resulting from the disclosed ponesimod regimens is particularly pronounced in patients having a lower baseline disability, e.g., a baseline expanded disability status scale (EDSS) score≤3.5 versus a baseline EDSS score>3.5, and, thus, in particular embodiments, the methods of treatment disclosed herein are directed to a sub-population of patients having an EDSS score of ≤3.5. Baseline refers to a time period prior to initiation of treatment with ponesimod and/or standard of care treatment. This time period is typically up to about 45 days prior to initiation of treatment, including, for example, up to about 40 days, up to about 35 days, up to about 30 days, up to about 25 days, up to about 20 days, up to about 15 days, or up to about 10 days prior to initiation of treatment with ponesimod and/or standard of care treatment.

In certain embodiments, the methods of reducing corticosteroid use disclosed herein are directed to patients having an EDSS score of ≤3.0.

In certain aspects, the methods are directed to patients that have had no prior disease modifying treatment (DMT) for multiple sclerosis, or no DMT for multiple sclerosis within about two years prior to initiation of treatment with ponesimod. In some embodiments, the methods are directed to patients that have had no prior DMT for multiple sclerosis, or no DMT for multiple sclerosis within about two years prior to initiation of treatment with ponesimod, and that have a baseline EDSS score of ≤3.5, including a baseline EDSS score of ≤3.0.

In some aspects, the methods of the disclosure are performed on a human patient suffering from multiple sclerosis. In some embodiments, the patient's multiple sclerosis is relapsing multiple sclerosis. In other embodiments, the relapsing multiple sclerosis comprises relapsing-remitting disease, clinically isolated syndrome, or active secondary progressive disease.

In some aspects of the methods of the present disclosure, the patient is administered an effective regimen of ponesimod. An effective regimen is one that elicits the biological or medicinal response in a human tissue system that is being sought by a researcher, medical doctor, or other clinician, which includes alleviation of one or more symptoms of the disease or disorder being treated.

As used herein, the term "ponesimod" refers to the compound (R)-5-[3-chloro (2,3-dihydroxy-propoxy)-benz[Z]ylidene]-2-([Z]-propylimino)-3-o-tolyl-thiazolidin-4-one, which has the following structure:

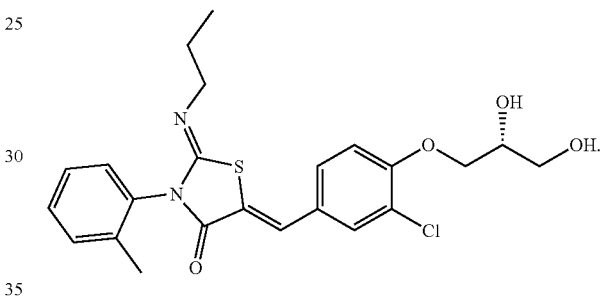

In some embodiments, "ponesimod" also refers to pharmaceutically acceptable salts of ponesimod. The term "pharmaceutically acceptable salt" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example Handbook of Pharmaceutical Salts. Properties, Selection and Use, P. Heinrich Stahl, Camille G. Wermuth (Eds.), Wiley-VCH, 2008 and Pharmaceutical Salts and Co-crystals, Johan Wouters and Luc Quere (Eds.), RSC Publishing, 2012.

It is to be understood that the present disclosure encompasses ponesimod in any form including amorphous as well as crystalline forms. It is further to be understood that crystalline forms of ponesimod encompasses all types of crystalline forms including polymorphs, solvates and hydrates, salts and co-crystals (when the same molecule can be co-crystallized with different co-crystal formers) provided they are suitable for pharmaceutical administration. In some embodiments, ponesimod is in crystalline form A or crystalline form C as described in WO 2010/046835, incorporated herein by reference. In some embodiments, ponesimod is in crystalline form C.

It should be noted that the amounts of ponesimod described herein are set forth on a ponesimod free base basis. That is, the amounts indicate that amount of the ponesimod molecule administered, exclusive of, for example, solvent (such as in solvates) or counterions (such as in pharmaceutically acceptable salts).

In some embodiments, the effective regimen comprises a daily dose of ponesimod. In some embodiments, the daily dose of ponesimod is administered orally.

In some embodiments, the daily dose of ponesimod is administered once daily.

In some embodiments, the daily dose of ponesimod is about 15 to about 25 mg. In further embodiments, the daily dose of ponesimod is about 15 mg, about 16 mg, about 17 mg, about 18 mg, about 19 mg, about 20 mg, about 21 mg, about 22 mg, about 23 mg, about 24 mg, or about 25 mg. In certain embodiments, the daily dose of ponesimod is about 20 mg.

In some embodiments, about 20 mg of ponesimod is administered orally once daily.

In other embodiments, the effective regimen comprises an up-titration, followed by a daily maintenance dose of ponesimod. An up-titration is a dosing procedure in which the daily dose of ponesimod is gradually increased over a period of days, culminating with administration of the maintenance dose.

In some embodiments, the regimen comprises an up-titration at the initiation of the method of the disclosure. In other embodiments, the regimen comprises an up-titration upon re-initiation of the method after a discontinuation of the method of the disclosure. As used herein, "upon re-initiation of the method after a discontinuation" means an interruption of the administration of ponesimod of at least one, at least two or preferably at least 3 days before treatment is re-initiated. In some embodiments, the regimen comprises an up-titration step at initiation of the method or upon re-initiation of the method after a discontinuation.

In some embodiments of the methods of the disclosure, the up-titration regimen one disclosed in U.S. Pat. No. 10,220,023, incorporated herein by reference. For example, in certain aspects, the up-titration comprises administering orally once daily about 2 mg of ponesimod on days 1 and 2; about 3 mg of ponesimod on days 3 and 4; about 4 mg of ponesimod on days 5 and 6; about 5 mg of ponesimod on day 7; about 6 mg of ponesimod on day 8; about 7 mg of ponesimod on day 9; about 8 mg of ponesimod on day 10; about 9 mg of ponesimod on day 11; and about 10 mg of ponesimod on days 12, 13, and 14.

In other embodiments of the methods of the disclosure, the up-titration comprises administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; 9 mg of ponesimod on day 11; and 10 mg of ponesimod on days 12, 13, and 14.

In some embodiments, the maintenance dose is about 20 mg of ponesimod once daily.

In some embodiments, the regimen comprises an up-titration step at initiation of the method or upon re-initiation of the method after a discontinuation, comprising administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; and 9 mg of ponesimod on day 11; 10 mg of ponesimod on days 12, 13, and 14, followed by the administering of the 20 mg of ponesimod once daily thereafter.

As disclosed and exemplified herein, the methods of the present disclosure provide health care providers with options for improved outcomes compared to standard of care. As used herein, the term "standard of care treatment" refers to a physician-prescribed treatment of MS. In some embodiments, the standard of care comprises, consists of, or consists essentially of administering an MS treatment that has been approved by a regulatory authority. In some embodiments, the standard of care treatment is Interferon (IFN) β-1a 30 mcg i.m. once weekly (Avonex®), IFN β-1a 22 or 44 mcg s.c. 3 times weekly (Rebif®), IFN β-1b 250 mcg s.c. every other day (Betaferon®, Extavia®), Pegylated IFN β-1a 125 mcg subcutaneously every 2 weeks (Plegridy®), Glatiramer acetate 20 mg s.c. once a day (o.d.) or 40 mg subcutaneously 3 times weekly (Copaxone®), Glatiramer acetate 20 mg s.c. o.d. (Glatopa®), Natalizumab 300 mg i.v. every 4 weeks (Tysabri®), Mitoxantrone i.v. every 3 months (Novantrone®), Alemtuzumab concentrate for solution for infusion, 12 mg alemtuzumab in 1.2 mL (10 mg/mL) (Lemtrada®), Fingolimod 0.5 mg orally o.d. (Gilenya®), Teriflunomide 7 mg, 14 mg o.d. (Aubagio®), Dimethyl fumarate (BG-12) gastro-resistant hard capsules 120/240 mg twice daily (Tecfidera®), or Cladribine 40 to 100 mg orally per treatment week (Mavenclad®).

In some embodiments, the standard of care treatment comprises a SW receptor modulator that is not ponesimod.

In other embodiments, the standard of care treatment comprises teriflunomide. In some embodiments, the standard of care treatment comprises administration of about 14 mg of teriflunomide orally once daily.

The present disclosure also provides pharmaceutical products comprising ponesimod. Typically, the pharmaceutical product is a package or is packaged, for example, a bottle, a pouch, or a blister pack.

In some embodiments, the package includes instructions. In certain embodiments, instructions are for administering ponesimod to a human patient suffering from multiple sclerosis in a regimen that is effective to reduce corticosteroid use in the management of the multiple sclerosis. In other embodiments, the package provides instructions and/or corticosteroid use data directed to patients having had no prior DMT for multiple sclerosis and/or patients having a baseline EDSS score of ≤3.5. In yet other embodiments, the package provides instructions and/or corticosteroid use data directed to patients having a baseline EDSS score of ≤3.0.

As used herein, the term "statistically significant" refers to the likelihood that a relationship between two or more variables is caused by something other than chance. A p-value less than 0.05 (typically ≤0.05) is a common metric for statistical significance and is indicative of strong evidence against the null hypothesis, as there is less than a 5% probability the null is correct (and the results are random).

The following Example is provided to illustrate some of the concepts described within this disclosure. While the Example is considered to provide an embodiment, it should not be considered to limit the more general embodiments described herein.

Example 1

Study Design

A prospective, multicenter, randomized, double-blind, active controlled, parallel-group, phase III, superiority study was conducted. The study was designed to compare the efficacy, safety, and tolerability of ponesimod 20 mg vs teriflunomide 14 mg in adult subjects with relapsing MS (OPTIMUM study (NCT02425644)).

Randomization: Subjects were randomized in a 1:1 ratio to ponesimod 20 mg or teriflunomide 14 mg, stratified by prior use of MS disease modifying treatment (DMT) in the last two years prior to randomization (yes, no) and by baseline expanded disability status scale (EDSS) score (EDSS≤3.5, EDSS>3.5).

Inclusion Criteria

This study enrolled adult male and female subjects aged 18 to 55 years with established diagnosis of MS, as defined by the 2010 revision of McDonald Diagnostic Criteria [Polman C H, et al. *Diagnostic criteria for multiple sclerosis: 2010 revisions to the McDonald criteria*. Ann Neurol. 2011; 69(2):292-302], with relapsing course from onset (i.e., relapsing-remitting multiple sclerosis and secondary progressive multiple sclerosis [SPMS] with superimposed relapses). The trial included up to a maximum 15% of subjects with SPMS with superimposed relapses.

Subjects had active disease evidenced by one or more MS attacks with onset within the period of 12 to 1 months prior to baseline EDSS assessment, or by two or more MS attacks with onset within the 24 to 1 months prior to baseline EDSS assessment, or with one or more gadolinium-enhancing (Gd+) lesion(s) of the brain on an MRI performed within 6 months prior to baseline EDSS assessment. Enrolled subjects were ambulatory with an EDSS score of up to 5.5 inclusive. The subjects were treatment-naïve (i.e., no MS disease-modifying therapy received at any time in the past) or previously treated with interferon (IFN) β-1a, IFN β-1b, glatiramer acetate, dimethyl fumarate, or natalizumab.

Exclusion Criteria:

Subjects with significant medical conditions or therapies for such conditions (e.g., cardiovascular, pulmonary, immunological, hepatic, ophthalmological, ocular) or lactating or pregnant women were not eligible to enter the study.

Subjects with contraindications to MRI or with clinically relevant medical or surgical conditions that, in the opinion of the investigator, would put the subject at risk by participating in the study were not eligible to enter the study.

Study/Treatment Duration:

For an individual subject, the maximum duration of the study was approximately 118 weeks consisting of 6 weeks of screening, 108 weeks of treatment and 4 weeks of safety follow-up. Subjects discontinuing treatment prematurely had an option to stay in a post-treatment observation period (PTOP) for up to 108 weeks.

The study consisted of the following periods:

Pre-randomization period—Up to 45 days before randomization.

Treatment period: The double-blind treatment period lasted for 108 weeks. It consisted of a randomization visit, visits at two, four, and 12 weeks after randomization, and 12-weekly visits thereafter.

End-of-Treatment (EOT):

The EOT visit took place at Week 108 (or earlier in case of premature discontinuation of study drug). In all cases, the EOT visit took place one day after the last dose of study drug but no later than 7 days after the last dose of study drug.

Subjects who completed treatment until Week 108 were eligible to enroll in an extension study conducted under a separate protocol. Subjects who discontinued study drug prematurely for any reason were not eligible for the extension study.

Subjects who prematurely discontinued study drug treatment were subsequently treated according to local standard of care at the investigator's discretion and were followed in the post-treatment observation period.

Post-Treatment Safety Follow-Up (FU) Period:

Teriflunomide is eliminated slowly from plasma. An accelerated elimination procedure was used by all subjects after the last dose of study drug. A safety FU after the last dose of study drug was mandated.

All subjects entered the safety FU period:

For subjects who entered the extension study, the FU period started after the last dose of study drug and ended with a safety FU visit (FU1) 14-22 days after the last dose of study drug or with an abbreviated FU2 23-37 days after the last dose of study drug (if compliance to the teriflunomide accelerated elimination procedure was assessed as not sufficient at FU1).

For subjects who did not enter the extension study, the safety FU period lasted for 30 days after the last dose of study drug and included two safety FU visits (FU1, FU2) at 14-22 and 30-37 days after the last dose of study drug, respectively.

Post-Treatment Observation Period (PTOP):

Subjects who prematurely discontinued study treatment enter the PTOP which lasts until 108 weeks after randomization (i.e., planned EOT period). It consisted of an abbreviated schedule of assessments at the time of the originally scheduled 12-weekly visits.

End-of-Study (EOS)

EOS was reached when treatment, safety FU, and, if applicable, PTOP have been completed.

For subjects who completed the 108-week treatment period and entered the extension study, the EOS visit corresponded to the FU visit (FU1) conducted 14-22 days after the last study drug dose or to the abbreviated FU2 visit conducted 23-37 days after the last study drug dose (if needed for compliance reasons with the teriflunomide accelerated elimination procedure).

For all other subjects, the EOS visit corresponded to the 30-day FU visit (FU2) or to the last visit of PTOP (i.e., Week 108 Visit of the PTOP), whichever was last.

Study Treatment:

The treatment period consisted of an up-titration period (from Day 1 to 14) and a maintenance period (Day 15 until EOT).

During an initial phase of the study, the study drugs in the up-titration period were administered in a double-dummy fashion. Ponesimod (or matching placebo) was presented as tablet, and teriflunomide 14 mg (or matching placebo) was presented as capsule (i.e., daily administration of one tablet and one capsule). At a later phase, the double-dummy material (tablet and capsule) was replaced by the daily administration of one capsule containing either ponesimod or teriflunomide.

In the maintenance period, the study treatment consisted of the daily administration of one capsule containing ponesimod 20 mg or teriflunomide 14 mg.

To reduce the first-dose effect of ponesimod, an up-titration scheme was implemented from Day 1 to Day 14:

Days 1 and 2; 2 mg.
Days 3 and 4; 3 mg.
Days 5 and 6; 4 mg.
Day 7; 5 mg.
Day 8; 6 mg.
Day 9; 7 mg.
Day 10; 8 mg.
Day 11; 9 mg.
Days 12, 13, and 14; 10 mg.
Day 15 until EOT; 20 mg.

Primary analysis set for efficacy: The Full Analysis Set (FAS) included all randomized subjects. Subjects were evaluated according to the treatment they were randomized to.

Primary efficacy variable/primary timepoint: The primary endpoint was annualized relapse rate (ARR) up to the end of study (EOS) defined as the number of confirmed relapses per subject-year. All available data up to EOS, regardless of treatment discontinuation was included (ITT approach).

Co-Administration of Ponesimod with Corticosteroids

In the phase 3 OPTIMUM study (NCT02425644), PON 20 mg demonstrated superior efficacy vs teriflunomide (TER) 14 mg in reducing annualized relapse rate (ARR) in patients with relapsing multiple sclerosis (RMS). Therapy with systemic corticosteroids (SCS) is commonly used for acute treatment of relapses in patients with RMS. However, use of high doses of SCS can lead to unwanted adverse events and tolerability issues. Prolonged treatment can also lead to steroid resistance and may have negative impacts on remyelination.

Objective

To compare the use of SCS for the treatment of relapses between PON and TER groups in the OPTIMUM trial.

Methods

OPTIMUM was a phase 3, double-blind, randomized clinical trial that evaluated the efficacy, safety, and tolerability of PON (20 mg) versus TER (14 mg) in patients with RMS. The OPTIMUM study is summarized in FIG. 1.

Patients with RMS aged 18 to 55 years with a relapsing course (i.e., RMS or secondary progressive MS with superimposed relapses), an Expanded Disability Status Scale (EDSS) score of 0 to 5.5, and recent clinical or magnetic resonance imaging activity were enrolled.

Patients were excluded from the primary analysis if they received treatment with SCS, unless it was for a multiple sclerosis (MS) relapse or short-term treatment of pulmonary conditions.

In this analysis, the proportions of patients in each treatment group who received concomitant treatment with ≥1 SCS to treat MS relapse between the start of study treatment and end of study (EOS) were compared. In addition, the mean accumulated steroid dose (prednisone equivalent doses in mg) administered to treat relapse between start of study treatment and EOS and between end of treatment (EOT) plus follow-up time was assessed.

Data are shown for analyses of the full analysis set and analyses stratified by baseline EDSS score (baseline EDSS score≤3.5 versus >3.5), prior MS treatment (disease-modifying treatment [DMT] within the past 2 years versus no DMT within the past 2 years), or sex (male versus female).

Statistical Analyses

The proportion of patients who received ≥1 SCS therapy for treatment of relapse is provided by treatment group; group differences were examined using Cochran-Mantel-Haenszel (CMH) test and stratified by baseline EDSS and prior treatment with DMT.

The between-group difference for the mean accumulated steroid dose for treatment of relapse was evaluated using analysis of covariance models with accumulated steroid dose as the dependent variable, treatment as factor, and EDSS baseline group, and prior treatment with disease-modifying therapy within 2 years prior to randomization as covariates. EDSS baseline group was removed from the model for analyses stratified by baseline EDSS score.

Results

Baseline Demographics and Disease Characteristics

Among 1133 patients, 567 received PON (20 mg) and 566 received TER (14 mg). Baseline demographics and disease characteristics were similar between the 2 treatment groups, summarized below in Table 1.

TABLE 1

Baseline Demographics and Disease Characteristics in Full Analysis Set

| | Patients, n (%) Ponesimod, 20 mg (n = 567) | Patients, n (%) Teriflunomide, 14 mg (n = 566) |
|---|---|---|
| Female | 363 (64.0) | 372 (65.7) |
| Age, mean (SD), years | 36.7 (8.74) | 363 (64.0) |
| Baseline EDSS > 3.5 | 94 (16.6) | 363 (64.0) |
| DMT within 2 years prior to randomization | 213 (37.6) | 363 (64.0) |
| Number of relapses in last year prior to study entry, mean (SD) | 1.2 (0.61) | 363 (64.0) |
| Highly active disease[a] | 202 (35.6) | 363 (64.0) |

[a]≥2 relapses within the 1 year prior to study entry, a baseline Expanded Disability Status Scale score > 2, and baseline magnetic resonance imaging of ≥1 gadolinium-enhancing T1 lesion; or any disease-modifying treatment received within 12 months prior to randomization and 1 or both of the following: (1) ≥1 relapse within 1 year prior to study entry and baseline magnetic resonance imaging either with ≥1 gadolinium-enhancing T1 lesion and/or 9 or more T2-weighted lesions or (2) a number of relapses within 1 year prior to study entry equal to or greater than the number of relapses between 2 years and 1 year prior to study entry, for patients with ≥1 relapse within the 2 years prior to study entry.

Concomitant Steroids and Accumulated Steroid Dose

In the full analysis set, a significantly smaller proportion of patients in the PON group compared with the TER group received ≥1 SCS therapy for treatment of relapse (29.1% versus 40.1%, respectively; P<0.0001). The results are shown in FIG. 2.

Figure 2:
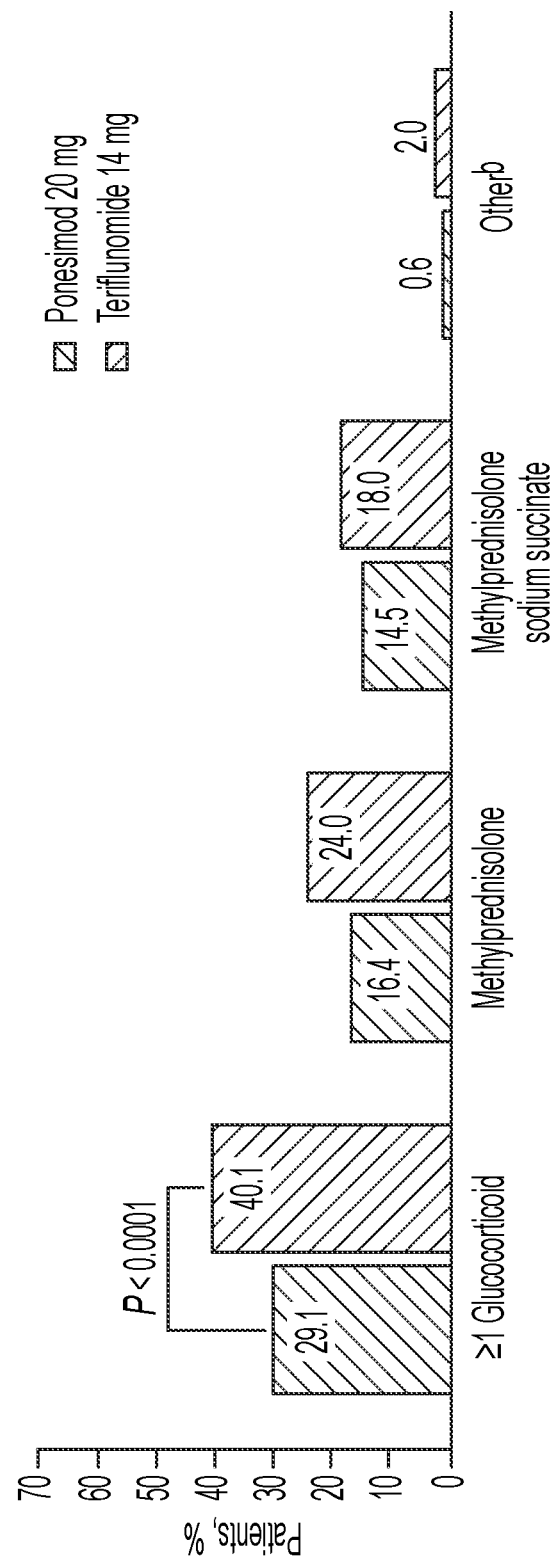
FIG. 2 depicts a bar graph of the proportion of patients receiving concomitant SCS for treatment of relapse between study treatment start and end-of-study (EOS) for ponesimod and teriflunomide.

In FIG. 2, patients were allowed to be on multiple SCS therapies over the course of the study such that the sum of patient proportions for each SCS (e.g., methylprednisolone) may be larger than the proportion shown for the overall glucocorticoid class (i.e., ≥1 glucocorticoid). Individual SCS therapies shown are based on WHO-DRUG dictionary, March 2018 version. For patients with multiple therapies coded by the same term (e,g., methylprednisolone), the term was counted only once for each patient. Therapies shown include those ongoing at study treatment start as well as therapies initiated between treatment start and EOS. Others include dexamethasone, hydrocortisone, prednisolone, prednisolone sodium succinate, and prednisone.

Figures 3A, 3B:
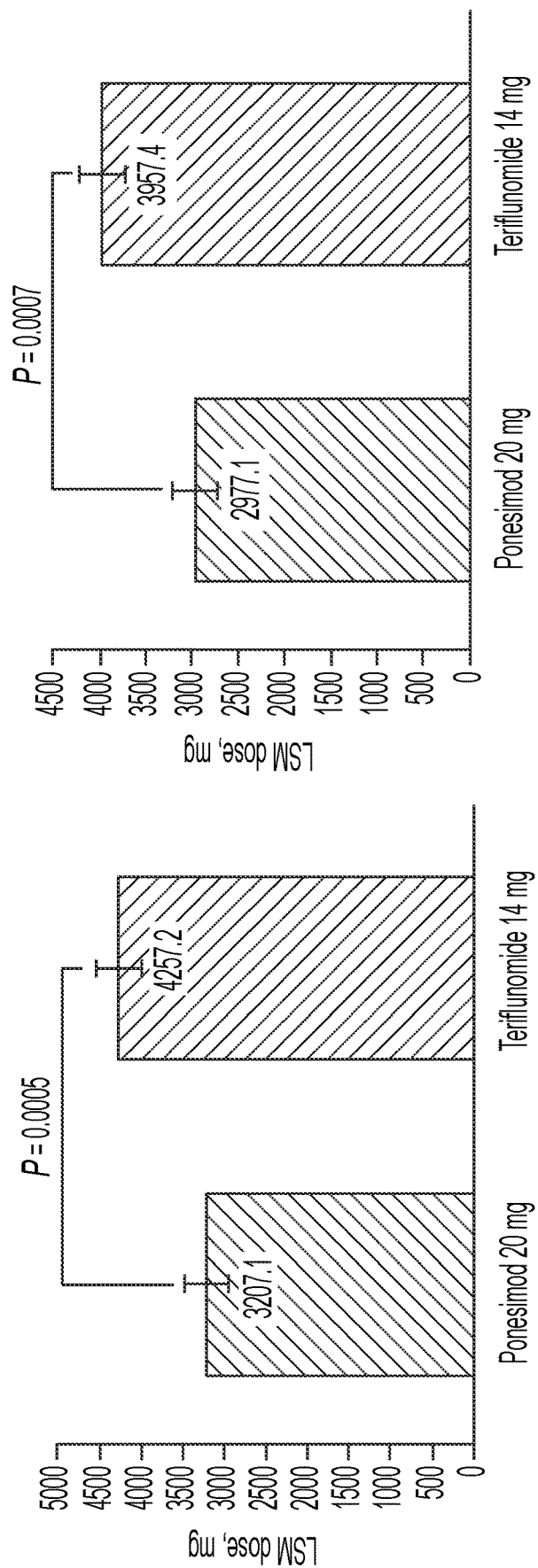
FIG. 3 depicts a bar graph of the accumulated steroid dose for treatment of relapse at (FIG. 3-A) EOS and (FIG. 3-B) EOT+7 days for ponesimod and teriflunomide.

FIG. 3 shows the least squares mean of accumulated steroid dose (prednisone equivalent doses in mg) for treatment of relapse was 3207.1 mg and 4257.2 mg in the PON and TER groups, respectively (P=0.0005) from start of study treatment to EOS (FIG. 3-A) and 2977.1 mg and 3957.4 mg in the PON and TER groups, respectively, (P=0.0007) from start of study treatment to EOT+7 days of follow up (FIG. 3-B).

In FIG. 3, patients without steroid use for treatment of relapses in the respective period are assigned 0 mg. Only steroids taken after study treatment start up to the specified time point for treatment of relapse were considered. Error bars represent standard error.

Results Stratified by Baseline Disability (EDSS), Prior Treatment, or Sex

Figure 4A:
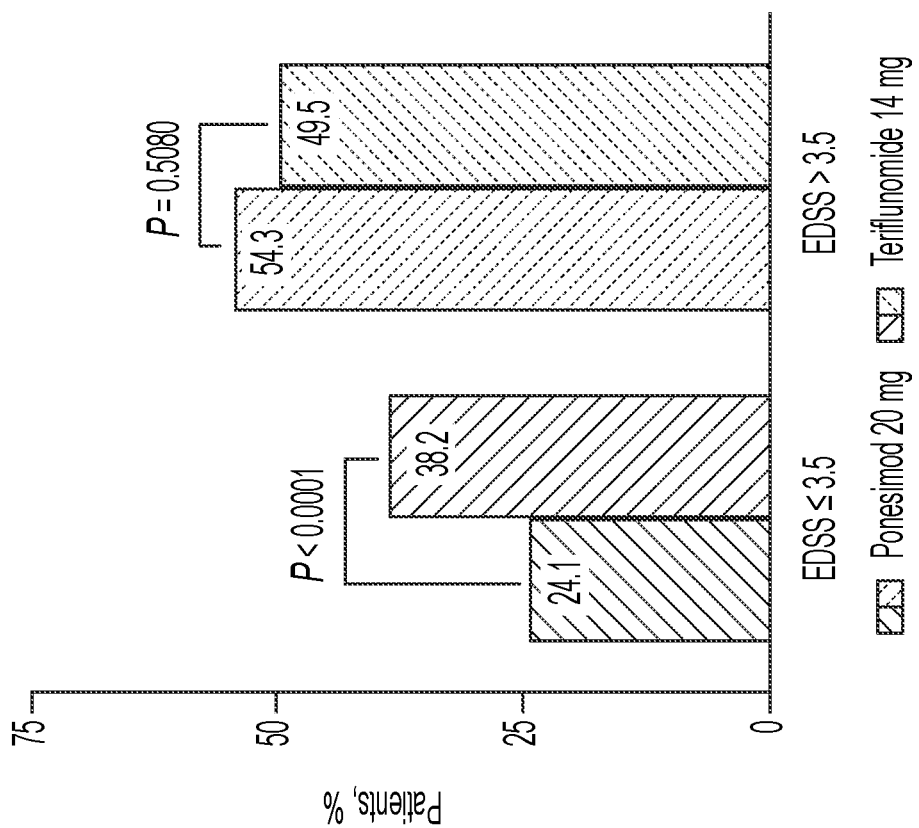
FIG. 4 depicts a bar graph of results stratified by baseline EDSS score for ponesimod and teriflunomide.
Figure 4B:
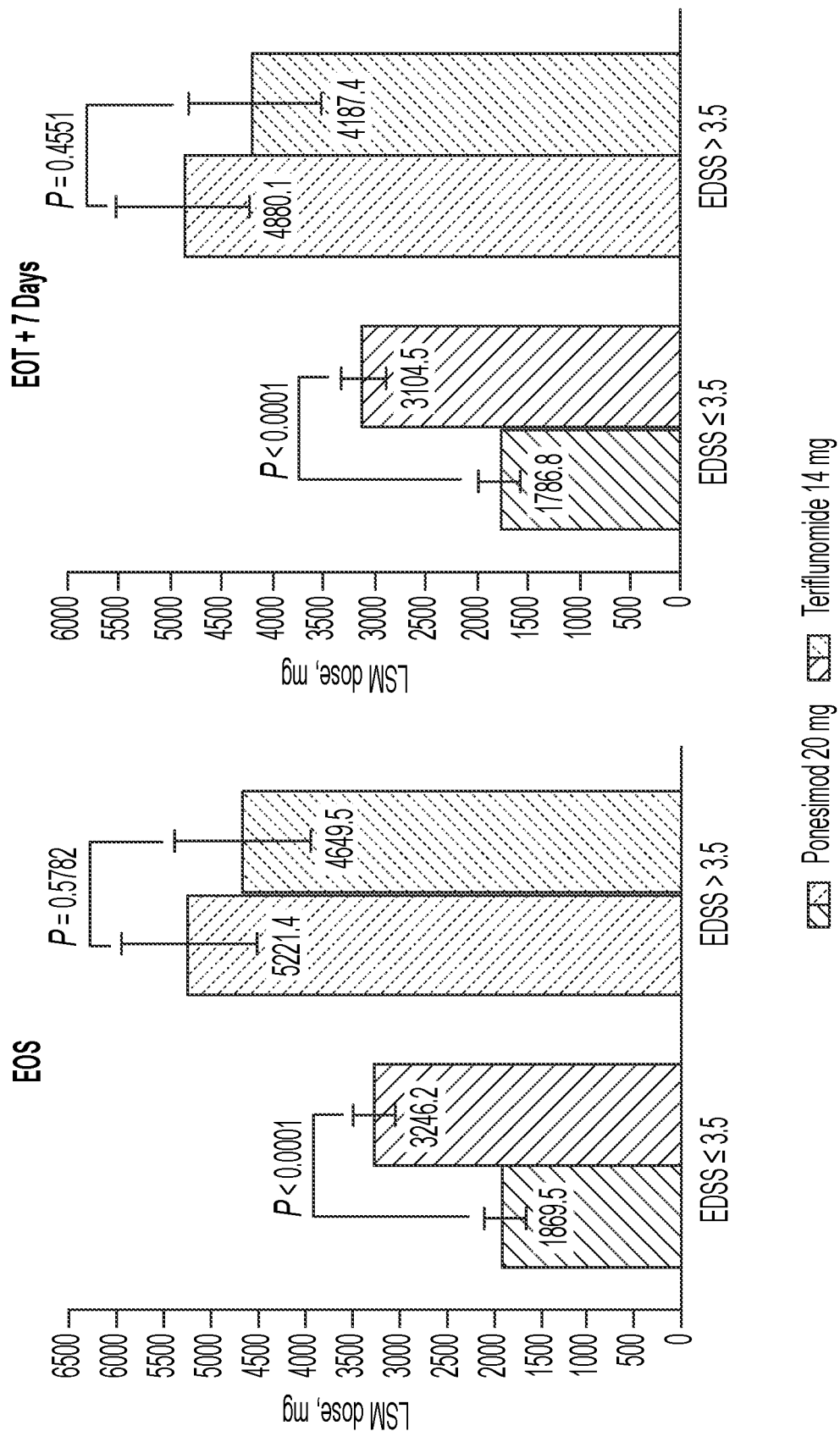

When patients were stratified by EDSS score (baseline EDSS score≤3.5 versus >3.5), significant differences between treatment groups were observed only for patients with EDSS score≤3.5, as shown in FIG. 4. In FIG. 4, patients were allowed to be on multiple SCS therapies at one time. Therapies include those ongoing at study treatment start as well as therapies initiated between treatment start and EOS. Patients without steroid use for treatment of relapses in the respective period are assigned 0 mg. Only steroids taken after study treatment start up to the specified time point for treatment of relapse were considered. Error bars represent standard error.

A significant treatment by EDSS strata interaction was observed for accumulated steroid dose, showing that the impact of treatment on accumulated steroid dose was dependent on EDSS strata.

Prior DMT within Past Two Years

Figure 5A:
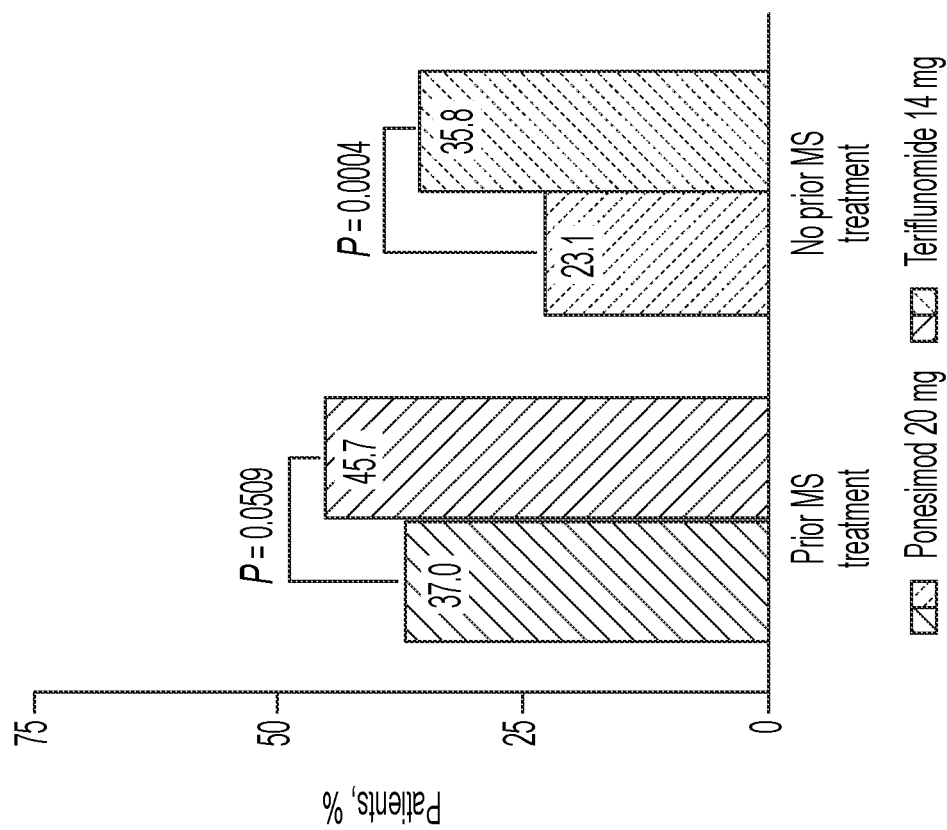
FIG. 5 depicts a bar graph of results stratified by prior MS treatment for ponesimod and teriflunomide.
Figure 5B:
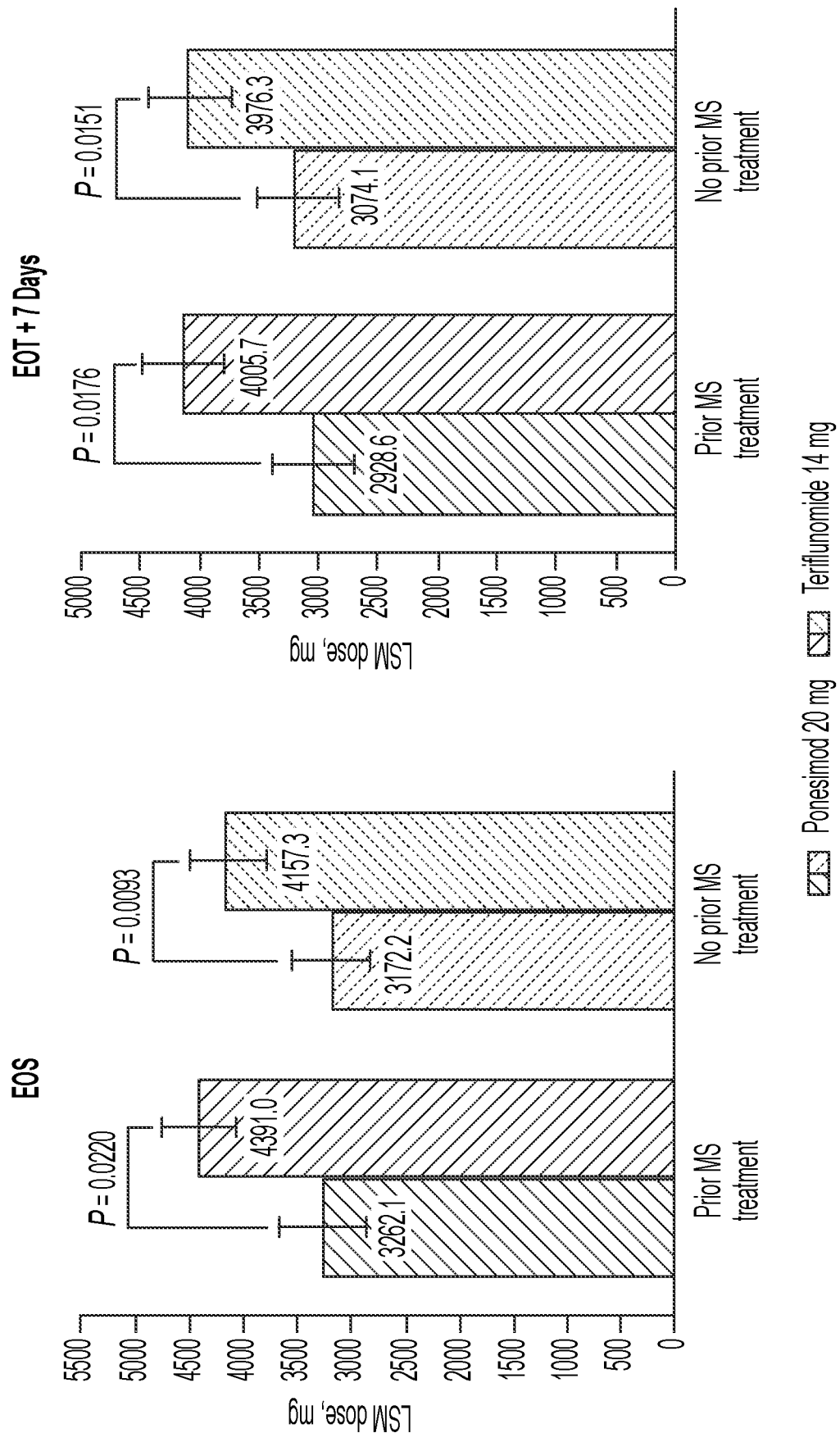

Results of the analysis stratified by prior MS treatment (DMT within the past 2 years versus no DMT within the past 2 years) were consistent with the overall analysis, with similar patterns observed in treatment-naïve and treatment-experienced groups, as shown in FIG. 5.

In FIG. 5, patients were allowed to be on multiple SCS therapies at one time. Therapies include those ongoing at study treatment start as well as therapies initiated between treatment start and EOS. Patients without steroid use for treatment of relapses in the respective period are assigned 0 mg. Only steroids taken after study treatment start up to the specified time point for treatment of relapse were considered. Error bars represent standard error.

Results Stratified by Sex

Figure 6A:
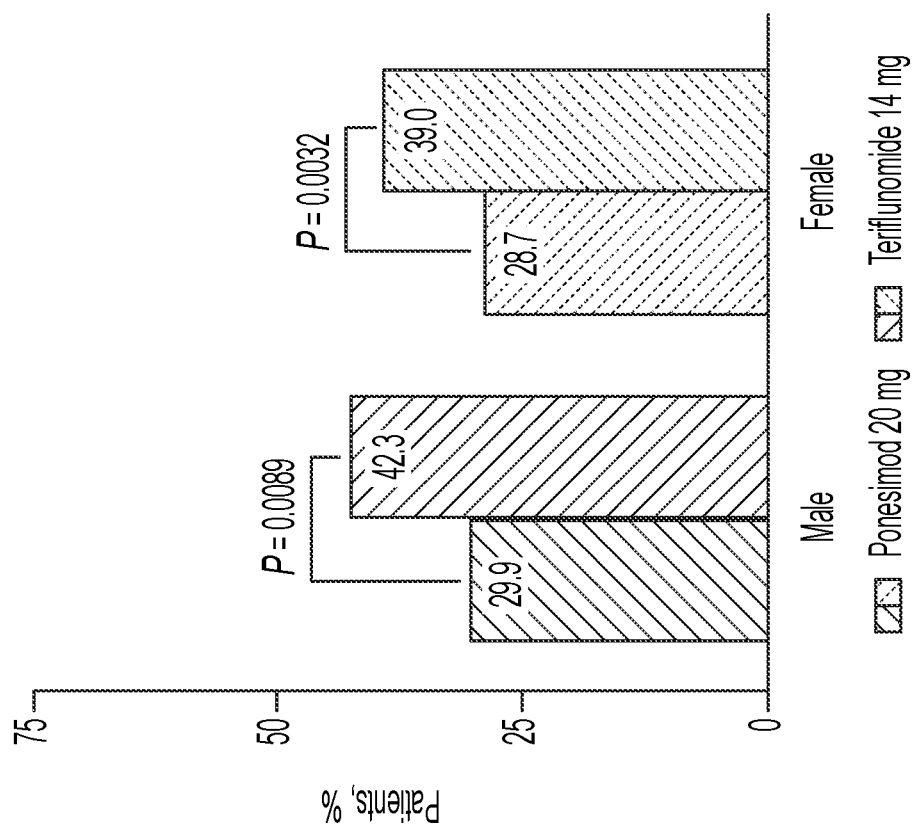
FIG. 6 depicts a bar graph of results stratified by sex for ponesimod and teriflunomide.
Figure 6B:
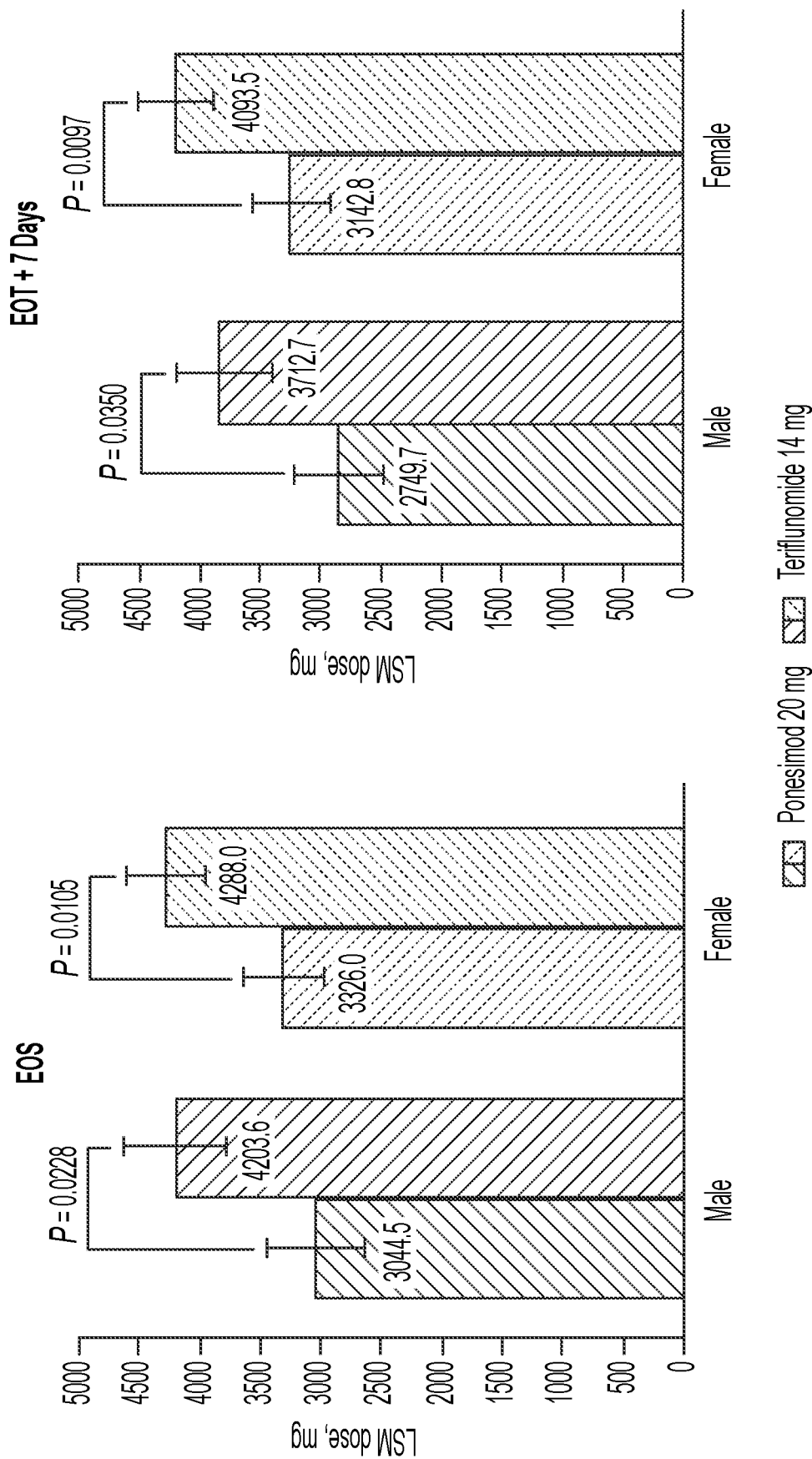

Results of the analysis stratified by sex (male versus female) were consistent with the overall analysis, with similar patterns observed in male and female patients, as shown in FIG. 6.

In FIG. 6, patients were allowed to be on multiple SCS therapies at one time. Therapies include those ongoing at study treatment start as well as therapies initiated between treatment start and EOS. Patients without steroid use for treatment of relapses in the respective period are assigned 0 mg. Only steroids taken after study treatment start up to the specified time point for treatment of relapse were considered. Error bars represent standard error.

CONCLUSIONS

A significantly smaller percentage of patients in the ponesimod group versus the teriflunomide group received at least 1 corticosteroid therapy for treatment of relapse. The mean accumulated steroid dose for treatment of relapse from start of study treatment to EOS was significantly lower in the ponesimod versus teriflunomide group.

When patients were stratified by baseline disability (EDSS≤3.5 versus >3.5), a significantly smaller proportion of patients in the ponesimod group received ≥1 SCS therapy compared with patients in the teriflunomide group only among patients with EDSS≤3.5. Results of analyses stratified by prior treatment and sex were consistent with findings of the overall analysis.

In sum, patients with RMS treated with ponesimod in the OPTIMUM trial achieved a lower rate of concomitant systemic corticosteroid use for the management of relapses compared with patients treated with teriflunomide; these findings were more pronounced in patients with lower baseline disability (EDSS≤3.5 versus EDSS>3.5).

What is claimed:

1. A method of reducing corticosteroid use in a patient with multiple sclerosis (MS), comprising:
   at initiation of the method or re-initiation of the method after discontinuation, administering orally once daily 2 mg of ponesimod on days 1 and 2; 3 mg of ponesimod on days 3 and 4; 4 mg of ponesimod on days 5 and 6; 5 mg of ponesimod on day 7; 6 mg of ponesimod on day 8; 7 mg of ponesimod on day 9; 8 mg of ponesimod on day 10; 9 mg of ponesimod on day 11; 10 mg of ponesimod on days 12, 13, and 14, followed by administering 20 mg of ponesimod orally once daily thereafter,
   wherein the patient has a baseline expanded disability status scale (EDSS) score of ≤3.5.

2. The method of claim 1, wherein the MS is relapsing multiple sclerosis.

3. The method of claim 2, wherein the relapsing multiple sclerosis comprises relapsing-remitting disease, clinically isolated syndrome, or active secondary progressive disease.

4. The method of claim 1, wherein the patient has had no prior disease modifying treatment (DMT) for multiple sclerosis.

5. The method of claim 1, wherein the patient has had no prior disease modifying treatment (DMT) for multiple sclerosis within about two years prior to initiation of treatment with ponesimod.

6. The method of claim 1, wherein the patient has a baseline expanded disability status scale (EDSS) score of ≤3.0.

7. The method of claim 1, wherein the patient has had no prior disease modifying treatment (DMT) for multiple sclerosis and has a baseline expanded disability status scale (EDSS) score of ≤3.0.

8. The method of claim 1, wherein the patient has had no prior disease modifying treatment (DMT) for multiple sclerosis within about two years prior to initiation of treatment with ponesimod and has a baseline expanded disability status scale (EDSS) score of ≤3.0.

9. The method of claim 1, wherein the corticosteroid is glucocorticoid, methylprednisone, or methylprednisone sodium succinate.

10. In a method of treating a patient suffering from multiple sclerosis, the improvement comprising:
    selecting as said patient a patient who has a baseline expanded disability status scale (EDSS) score of ≤3.5; and
    administering to said patient a dose of ponesimod orally once daily according to an up-titration regimen comprising:
       2 mg of ponesimod on days 1 and 2;
       3 mg of ponesimod on days 3 and 4;
       4 mg of ponesimod on days 5 and 6;
       5 mg of ponesimod on day 7;
       6 mg of ponesimod on day 8;
       7 mg of ponesimod on day 9;
       8 mg of ponesimod on day 10;
       9 mg of ponesimod on day 11;
       10 mg of ponesimod on days 12, 13, and 14; and
       20 mg of ponesimod orally once daily thereafter,
    wherein the dose of ponesimod is effective to reduce corticosteroid use in said patient.

11. The improvement of claim 10, wherein the MS is relapsing multiple sclerosis.

12. The improvement of claim 11, wherein the relapsing multiple sclerosis comprises relapsing-remitting disease, clinically isolated syndrome, or active secondary progressive disease.

13. The improvement of claim 11, wherein the patient has had no prior disease modifying treatment (DMT) for multiple sclerosis within about two years prior to initiation of treatment with ponesimod.

* * * * *